(12) United States Patent
Ku et al.

(10) Patent No.: US 8,865,689 B2
(45) Date of Patent: Oct. 21, 2014

(54) METHODS AND COMPOSITIONS FOR TREATING HYPERURICEMIA AND METABOLIC DISORDERS ASSOCIATED WITH HYPERURICEMIA

(75) Inventors: Mannching Sherry Ku, Thiells, NY (US); Chih-Kuang Chen, Taipei (TW); Wei-Shu Lu, New Taipei (TW); I-Yin Lin, Taipei (TW)

(73) Assignee: TWi Biotechnology, Inc., Taipei (TW)

( * ) Notice: Subject to any disclaimer, the term of this patent is extended or adjusted under 35 U.S.C. 154(b) by 1 day.

(21) Appl. No.: 13/414,264

(22) Filed: Mar. 7, 2012

(65) Prior Publication Data

US 2012/0232044 A1 Sep. 13, 2012

Related U.S. Application Data

(60) Provisional application No. 61/451,600, filed on Mar. 11, 2011.

(51) Int. Cl.
| | |
|---|---|
| *A61K 31/222* | (2006.01) |
| *A61K 31/192* | (2006.01) |
| *A61P 19/06* | (2006.01) |
| *A61P 29/00* | (2006.01) |
| *A61K 31/56* | (2006.01) |
| *C07C 65/40* | (2006.01) |
| *C07C 69/16* | (2006.01) |
| *A61K 31/519* | (2006.01) |
| *A61K 31/52* | (2006.01) |

(52) U.S. Cl.
CPC ............. *A61K 31/222* (2013.01); *A61K 31/519* (2013.01); *A61K 31/52* (2013.01); *A61K 31/192* (2013.01)
USPC ........... 514/171; 514/510; 514/569; 562/461; 560/255

(58) Field of Classification Search
CPC ................ A61K 31/122; A61K 31/52; A61K 31/31192; A61K 31/519
See application file for complete search history.

(56) References Cited

U.S. PATENT DOCUMENTS

| 7,820,154 B2 | 10/2010 | Vicary et al. | |
| 2006/0074079 A1* | 4/2006 | Armenta et al. | ........... 514/226.5 |
| 2010/0104651 A1* | 4/2010 | Gao et al. | ....................... 424/489 |
| 2010/0150938 A1 | 6/2010 | Latz et al. | |

OTHER PUBLICATIONS

So et al. in Arthritis Research & Therapy, 9(2) 1-6 (2007).*
Pavelka et al. in Arthritis and Rheumatism, 56(12), 4055-4064 (2007).*
Dougados et al. in Arthritis and Rheumatism 44(11), 2539-2547 (2001).*
Dehgan et al. in Diabetes Care 31:361261-362, 2008.*
"gout definition" in www.google.com/search?q=gout+definition&sourceid=ie7&rls=com. microsoft:en-us:IE-Address&ie=&oe= (retrieved from the internet Feb. 5, 2014).*
Arthritis Advisory Committee Meeting; FDA Briefing Document Supplemental BLA 125319 (Jun. 21, 2009).*
Summary of Products Characteristics for Medicinal Product Canakinumab (Trade Name: Ilaris) in www.ema.europa.eu/docs/en_GB/document_library/EPAR_-_Product_Information/human/001109/WC500031680.pdf (Retrieved from the internet Jun. 11, 2014).*
A. So, A pilot study of IL-1 inhibition by anakinra in acute gout, Arthritis Research & Therapy 2007, 9:R28 (doi:10.1186/ar2143).

* cited by examiner

*Primary Examiner* — Dennis Heyer
(74) *Attorney, Agent, or Firm* — Wood, Phillips, Katz, Clark & Mortimer

(57) ABSTRACT

Methods and compositions for treating and/or preventing hyperuricemia or metabolic disorders associated with hyperuricemia comprising administering to a patient in need a therapeutically effective amount of diacerein, rhein, or a pharmaceutically acceptable salt, an analog, a prodrug, or an active metabolite thereof.

13 Claims, 2 Drawing Sheets

METHODS AND COMPOSITIONS FOR TREATING HYPERURICEMIA AND METABOLIC DISORDERS ASSOCIATED WITH HYPERURICEMIA

BACKGROUND OF THE INVENTION

Hyperuricemia is defined by values of blood uric acid over 6.8 to 7.0 mg/dL in men or over 6 mg/dL in women. Hyperuricemia and metabolic disorders associated with hyperuricemia, such as gout, affect 3 to 5 million individuals in the United States. In the United States, African Americans are twice as likely as Caucasian Americans to have gout. Further, gout and hyperuricemia have become common in China, Japan, Polynesia and urban sub-Saharan Africa, with rates of gout approximately doubling between 1990 and 2010. This rise in the incidence of the disease is believed to be due to a longer life expectancy, changes in diet, alcohol consumption and an increase in diseases associated with gout, such as metabolic syndrome, renal insufficiency and hypertension. A number of factors have been found to influence rates of gout, including age, race, and the season of the year. In men over the age of 30 and women over the age of 50, prevalence of gout is approximately two percent.

The metabolic disorders associated with hyperuricemia include not only gout, but also painful attacks of acute, monarticular, inflammatory arthritis due to uric acid crystals, deposition of urate crystals in joints, deposition of urate crystals in renal parenchyma, urolithiasis, nephrolithiasis and gouty nephropathy. Long term nephrolithiasis and gouty nephropathy are known to increase the risk of kidney damage and kidney failure.

Gout is a medical condition usually characterized by recurrent attacks of acute inflammatory arthritis. The metatarsalphalangeal joint at the base of the big toe is the most commonly affected (in about 50% of cases). However, gout may also present as tophi, kidney stones or urate nephropathy. Gout is believed to be caused by elevated levels of uric acid in the blood which crystallize and are deposited in joints, tendons, and surrounding tissues.

Current treatments for hyperuricemia and gout include lowering the blood concentration of uric acid by urate-lowering agents, such as: 1) xanthine oxidase inhibitors, such as allopurinol and febuxostat; 2) uricosuric agents, such as sulphinpyrazone, benzbromarone and probenecid; 3) urate oxidases, such as pegloticase, puricase, rasburicase and pegylated uricase; and 4) fenofibrate. In addition, the symptoms of acute gout may be controlled by anti-inflammatory agents, such as: 1) non-steroidal anti-inflammatory drugs (NSAIDs), such as indomethacin and ibuprofen; 2) corticosteroids; and 3) colchicine. Bringing the blood uric acid levels back to the normal range may decrease the incidence of the recurrent acute gout and prevent other metabolic disorders associated with hyperuricemia.

However, many of the currently available treatments for gout or hyperuricemia are associated with a variety of adverse side effects. For example, xanthine oxidase inhibitors, such as allopurinol, are associated with hypersensitivity angiitis, Stevens-Johnson syndrome, exfoliative dermatitis, plastic anemia, and hepatic insufficiency. Uricosuric agents, such as probenecid, bucolome and benzbromarone, have such side effects as gastrointestinal disorders, urinary lithiasis; and fulminant hepatic failure in patients with idiosyncrasies. Further, probenecid may affect the excretion of such drugs as captopril, indomethacin, ketoprofen, ketorolac, naproxen, cephalosporins, quinolones, penicillins, methotrexate, zidovudine, gancyclovir and acyclovir. Long term use of NSAIDs may lead to side effects, including ulcer perforation and upper gastrointestinal bleeding.

Therefore, there is still a need to develop new agents for the treatment of gout and hyperuricemia.

SUMMARY OF THE INVENTION

The present invention provides therapeutic methods for the treatment and/or prevention of hyperuricemia and metabolic disorders associated with hyperuricemia, such as gout, gout arthritis, gout flares, uric acid nephrolithiasis and gouty nephropathy. The methods are especially suitable for hyperuricemic patients who have inadequate medical control or cannot tolerate the currently available urate-lowering and anti-inflammatory therapies.

In particular, the methods of using a therapeutically effective amount of diacerein, rhein, or a pharmaceutically acceptable salt, an analog, a prodrug, or an active metabolite thereof to treat and/or prevent hyperuricemia and metabolic disorders associated with hyperuricemia offer unexpected advantages in decreasing the blood uric acid levels as compared to the use of the currently available pharmaceutical agents.

Diacerein, [4,5-bis(acetyloxy)-9,10-dioxo-2-anthracene carboxylic acid], is a highly purified anthraquinone derivative. It has been approved as a SYmptomatic Slow-Acting Drug in Osteoarthritis (SYSADOA) in several countries. Rhein is the major active metabolite of diacerein. Diacerein has been demonstrated to inhibit the synthesis and activity of proinflammatory cytokines such as interleukin-1 (IL-1), TNF-$\alpha$ and interleukin-6 (IL-6).

According to the present invention, diacerein can decrease and maintain blood uric acid levels within the normal range during the treatment period of patients with hyperuricemia and metabolic disorders associated with hyperuricemia. Further, diacerein can also prevent the recurrence of acute gout arthritis and gout flares, whether it is used as the sole active drug (i.e., diacerein monotherapy) or in a combination with other urate-lowering and/or anti-inflammatory agents.

Accordingly, in one embodiment, the invention provides a method of treating and/or preventing hyperuricemia or a metabolic disorder associated with hyperuricemia comprising administering to a patient in need thereof a therapeutically effective amount of a compound selected from the group consisting of: 1) diacerein, 2) rhein, and 3) a pharmaceutically acceptable salt, an analog, a prodrug, or an active metabolite thereof.

In another embodiment, the method of treating and/or preventing hyperuricemia or a metabolic disorder associated with hyperuricemia may further comprise administering to said patient at least one additional therapeutic agent selected from the group consisting of anti-inflammatory agents and urate-lowering agents.

In another embodiment, the invention provides a method of improving blood uric acid level control in a patient with gout, hyperuricemia or a metabolic disorder associated with hyperuricemia comprising administering to said patient a therapeutically effective amount of a compound selected from the group consisting of: 1) diacerein, 2) rhein, and 3) a pharmaceutically acceptable salt, an analog, a prodrug, or an active metabolite thereof.

In another embodiment, the invention provides a method of treating and/or preventing hyperuricemia or a metabolic disorder associated with hyperuricemia in a patient receiving a urate-lowering agent or an anti-inflammatory agent, comprising administering to said patient a therapeutically effective amount of a compound selected from the group consisting of:

1) diacerein, 2) rhein, and 3) a pharmaceutically acceptable salt, an analog, a prodrug, or an active metabolite thereof.

In yet another embodiment, the invention provides a method of treatment for hyperuricemia or a metabolic disorder associated with hyperuricemia in a patient with poor tolerance to therapeutic agents selected from the group consisting of anti-inflammatory agents and urate-lowering agents, comprising administering to said patient a therapeutically effective amount of a compound selected from the group consisting of: 1) diacerein, 2) rhein, and 3) a pharmaceutically acceptable salt, an analog, a prodrug, or an active metabolite thereof.

DETAILED DESCRIPTION OF THE INVENTION

Figure 1:
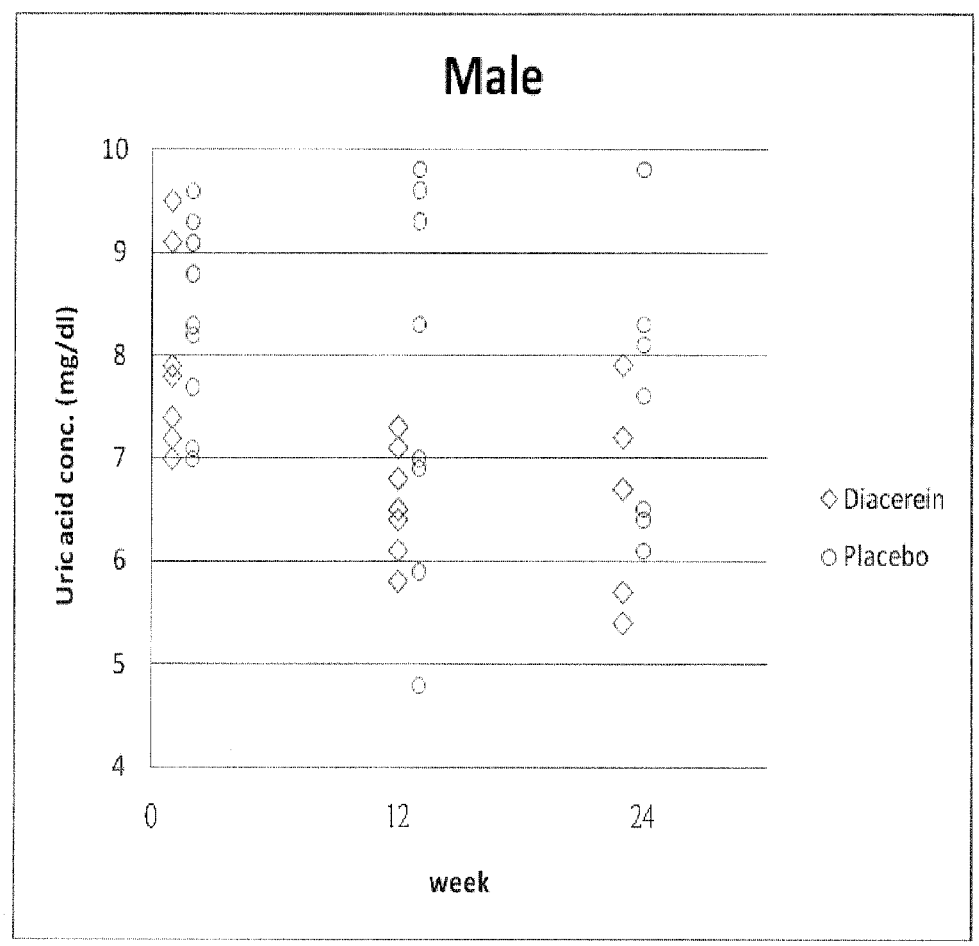
FIG. 1 is a graph demonstrating blood uric acid levels in male patients treated with either diacerein or placebo.

According to the present invention, diacerein, rhein, or a pharmaceutically acceptable salt, an analog, a prodrug, or an active metabolite thereof can be used for the treatment and/or prevention of hyperuricemia and metabolic disorders associated with hyperuricemia, such as gout, gout arthritis, gout flares, uric acid nephrolithiasis and gouty nephropathy.

Treatment of hyperuricemia aims to reduce the blood levels of uric acid to the normal range. In humans, the upper end of the normal range of blood uric acid levels is about 6 mg/dL for women and about 7.0 mg/dL for men. These ranges are subject to change depending on updated clinical guidelines. Treatment of gout aims to relieve pain and inflammation of the acute attack and reduce the incidence of recurrent attacks.

Use of diacerein, rhein and pharmaceutically acceptable salts, analogs, prodrugs, or active metabolites thereof to treat and/or prevent hyperuricemia and metabolic disorders associated with hyperuricemia, such as gout, offers unexpected advantages compared to the use of conventional treatments. These advantages include the ability to decrease blood uric acid levels and to prevent the recurrence of gout symptoms. In addition, in some embodiments of the invention, the methods of the present invention allow for oral administration of the drug, thus avoiding injection-site adverse reactions.

As used herein, diacerein (4,5-bis(acetyloxy)-9,10-dioxo-2-anthracene carboxylic acid) refers to a compound having the following structural formula:

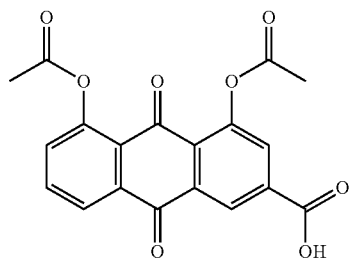 [SMILES: CC(=O)Oc1cccc2c1C(=O)c1c(OC(C)=O)cc(C(=O)O)cc1C2=O]

Diacerein directly inhibits IL-1β synthesis and modulates IL-1β induced activities. Diacerein has been shown to have disease modifying effect in experimental models of osteoarthritis and in human subjects with finger joint and knee osteoarthritis. IL-1β plays a fundamental role in osteoarthritis pathophysiology and cartilage destruction. IL-1β also promotes the expression of inducible nitric oxide synthase, and increases the release of prostaglandin E2, IL-6, IL-8 and TNF-α in human osteoarthritis chondrocytes.

Pharmaceutically acceptable salts, analogs, prodrugs and active metabolites of diacerein are also contemplated for use in this invention. Rhein (9,10-dihydro-4,5-dihydroxy-9,10-dioxo-2-anthracenecarboxylic acid) and monoacetylrhein are the known active metabolites of diacerein.

As used herein, the term "pharmaceutically acceptable salts" includes salts of acidic or basic groups. Examples of pharmaceutically acceptable salts include those derived from inorganic acids, such as hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids, such as acetic; propionic; isobutyric; maleic; malonic; benzoic; succinic; suberic; fumaric; mandelic; phthalic; benzenesulfonic; toluenesulfonic, including p-toluenesulfonic, m-toluenesulfonic, and o-toluenesulfonic; citric; tartaric; methanesulfonic; and the like. Also included are salts of amino acids such as arginate and the like, and salts of organic acids, such as glucuronic or galacturonic acids and the like.

As used herein, the term "prodrug" refers to a pharmacologically inactive derivative of an active drug designed to convert into the active drug through in vivo physiological action, such as hydrolysis, metabolism and the like.

As used herein, the term "urate-lowering agent" refers to a drug used to treat gout and hyperuricemia by lowering uric acid levels in the blood. Examples of the currently available urate-lowering agents include, but not limited to, 1) xanthine oxidase inhibitors, such as allopurinol and febuxostat; 2) uricosuric agents, such as sulphinpyrazone, benzbromarone and probenecid; 3) urate oxidase inhibitors, such as pegloticase, puricase, rasburicase and pegylated uricase; and 4) fenofibrate. Those drugs can be given alone or in a combination.

As used herein, the term "anti-inflammatory agent" refers to a drug used to treat inflammatory symptoms of gout and hyperuricemia. Examples of the currently available anti-inflammatory agents include, but not limited to, 1) non-steroidal anti-inflammatory drugs (NSAIDs), such as indomethacin and ibuprofen, 2) corticosteroids, and 3) colchicine.

As used herein, the terms "treatment" and "treating" include inhibiting the disease or condition, causing a reduction in severity and/or frequency of symptoms, elimination of symptoms and/or underlying cause, prevention of the occurrence of symptoms and/or their underlying cause, ameliorating and/or improving a patient's condition. Thus, "treating" a patient with said compositions of the invention includes prevention of a particular disorder in a susceptible individual, as well as management of a clinically symptomatic individual to inhibit or cause regression of a disorder or disease, and maintenance of the current state and/or prevention of a progression of a disorder or disease. Treatment can include prophylaxis, therapy, or cure.

As used herein, the term "therapeutically effective amount" of the compounds and/or pharmaceutical compositions of the invention refers to a sufficient amount of the compound and/or composition to treat, inhibit, ameliorate or prevent hyperuricemia or metabolic disorders associated with hyperuricemia, at a reasonable benefit/risk ratio applicable to any medical treatment. It will be understood, however, that the total daily usage of the compounds and/or compositions of the present invention will be decided by the attending physician within the scope of sound medical judgment. The specific effective dose level for any particular patient will depend upon a variety of factors, including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the composition at levels lower than required to achieve the desired therapeutic effect and to gradually increase the dosage until the desired effect is achieved.

As used herein, the term "co-administered" includes administration of diacerein and at least one urate-lowering agent and/or anti-inflammatory agent either as a single composition or as separate compositions. Diacerein and at least one urate-lowering agent and/or anti-inflammatory agent may be administered by the same or different routes of administration and/or at the same or different time or dosing regimens.

In one embodiment, the invention provides a method of treating and/or preventing hyperuricemia or a metabolic disorder associated with hyperuricemia comprising administering to a patient in need thereof a therapeutically effective amount of a compound selected from the group consisting of: 1) diacerein, 2) rhein, and 3) a pharmaceutically acceptable salt, an analog, a prodrug, or an active metabolite thereof.

In a preferred embodiment, the therapeutically effective amount of diacerein is from 10 to 200 mg per day. In another embodiment, the therapeutically effective amount of a pharmaceutically acceptable salt, an analog, a prodrug, or an active metabolite of diacerein is equivalent to from 10 to 200 mg of diacerein base per day.

In a preferred embodiment, the active metabolite of diacerein is monoacetylrhein or rhein.

In one embodiment, the metabolic disorder associated with hyperuricemia is selected from the group consisting of acute gout, chronic gout, gout arthritis, gout flares, uric acid nephrolithiasis and gouty nephropathy.

In one embodiment, the method of treating and/or preventing hyperuricemia or a metabolic disorder associated with hyperuricemia may further comprise administering to said patient at least one additional therapeutic agent selected from the group consisting of anti-inflammatory agents and urate-lowering agents.

In another embodiment, the invention provides a method of improving blood uric acid level control in a patient with gout, hyperuricemia or a metabolic disorder associated with hyperuricemia comprising administering to said patient a therapeutically effective amount of a compound selected from the group consisting of: 1) diacerein, 2) rhein, and 3) a pharmaceutically acceptable salt, an analog, a prodrug, or an active metabolite thereof.

In another embodiment, the invention provides a method of treating or preventing hyperuricemia or a metabolic disorder associated with hyperuricemia in a patient receiving a urate-lowering agent or an anti-inflammatory agent, comprising administering to said patient a therapeutically effective amount of a compound selected from the group consisting of: 1) diacerein, 2) rhein, and 3) a pharmaceutically acceptable salt, an analog, a prodrug, or an active metabolite thereof.

In a preferred embodiment, the method of treating or preventing hyperuricemia or a metabolic disorder associated with hyperuricemia in a patient receiving a urate-lowering agent or an anti-inflammatory agent reduces blood levels of uric acid below the upper end of the normal range in said patient.

However, in some embodiments, the provided methods of treating and/or preventing hyperuricemia or a metabolic disorder associated with hyperuricemia, as well as the provided methods of improving blood uric acid level control in a patient with gout, hyperuricemia or a metabolic disorder associated with hyperuricemia, do not require and do not comprise a co-administration of any additional therapeutic agents, including but not limited to, urate-lowering agents, anti-inflammatory agents, inhibitors of pH-activated proteases and others.

In another embodiment, the invention provides a method of treatment for hyperuricemia or a metabolic disorder associated with hyperuricemia in a patient with poor tolerance to therapeutic agents selected from the group consisting of anti-inflammatory agents and urate-lowering agents, comprising administering to said patient a therapeutically effective amount of a compound selected from: 1) diacerein, 2) rhein, and 3) a pharmaceutically acceptable salt, an analog, a prodrug, or an active metabolite thereof.

In a preferred embodiment, the anti-inflammatory agent is selected from the group consisting of non-steroidal anti-inflammatory drugs (NSAIDs), corticosteroids, colchicines and a combination thereof.

Examples of NSAIDs include, but are not limited to, arylalkanoic acids such as acetaminophen; 2-arylpropionic acids such as ibuprofen, ketorolac and naproxen; n-arylanthranilic acids such as mefenamic acid, meclofenamic acid; oxicams such as piroxicam, meloxicam; arylalkanoic acids such as diclofenac, etodolac, indomethacin, sulindac; and COX-2 inhibitors such as celecoxib.

In a preferred embodiment, the urate-lowering agent is selected from the group consisting of xanthine oxidase inhibitors, uricosuric agents, urate oxidases, urinary alkalinizers and fenofibrate.

Examples of xanthine oxidase inhibitors include, but are not limited to, allopurinol, oxypurinol and febuxostat. Examples of uricosuric agents include, but are not limited to, bucolome, sulphinpyrazone, benzbromarone and probenecid. Examples of urate oxidases include, but are not limited to, pegloticase, puricase, rasburicase, uricase and pegylated uricase. Examples of urinary alkalinizers include, but are not limited to, sodium hydrogen carbonate, potassium citrate and sodium citrate.

In a preferred embodiment, the method of treatment lowers blood levels of uric acid; and/or decreases inflammatory effects of gout arthritis and gout flares induced by hyperuricemia; and/or dissolves kidney stones; and/or reduces the recurrence rate of acute inflammatory arthritis induced by hyperuricemia; and/or prevents the recurrent hyperuricemia; and/or slows down the progression of urate nephropathy in said patient.

In another preferred embodiment, the method of treatment reduces blood levels of uric acid below the upper end of the normal range in said patient.

Diacerein and an anti-inflammatory agent and/or a urate-lowering agent may be contained in a single formulation or may be co-administered as separate formulations.

The invention also provides pharmaceutical compositions for treating and/or preventing hyperuricemia or a metabolic disorder associated with hyperuricemia in a patient comprising a therapeutically effective amount of a compound selected from the group consisting of: 1) diacerein, 2) rhein, and 3) a pharmaceutically acceptable salt, an analog, a prodrug, or an active metabolite thereof.

In a preferred embodiment, the therapeutically effective amount of diacerein is from 10 to 200 mg per day. In another embodiment, the therapeutically effective amount of a pharmaceutically acceptable salt, an analog, a prodrug, or an active metabolite of diacerein is equivalent to from 10 to 200 mg of diacerein base per day.

The invention also provides pharmaceutical compositions comprising: 1) diacerein, rhein, or a pharmaceutically acceptable salt, a prodrug, or an active metabolite thereof, and 2) at least one additional therapeutic agent.

In one embodiment, the additional therapeutic agent is selected from the group consisting of anti-inflammatory agents and urate-lowering agents.

In a preferred embodiment, the additional therapeutic agent is selected from the group consisting of: 1) xanthine oxidase inhibitors; 2) uricosuric agents; 3) urate oxidase inhibitors; 4) fenofibrate; 5) NSAIDs; 6) corticosteroids, and 7) colchicine.

The additional active ingredient can be present in a controlled-release dosage form or in an immediate release dosage form.

When administered to a patient in need thereof, diacerein, its pharmaceutically acceptable salts, prodrugs, or active metabolites can be prepared as pharmaceutical compositions.

The pharmaceutical composition can further include a pharmaceutically acceptable carrier, and can be in solid or liquid form, including but not limited to, tablets, powders, capsules, pellets, solutions, suspensions, elixirs, emulsions, gels, creams, patch, or suppositories, including rectal and urethral suppositories.

As used herein, the term "pharmaceutically acceptable carrier" refers to a pharmaceutically acceptable material, composition or vehicle, such as a liquid or solid filler, diluent, excipient, solvent or encapsulating material. A pharmaceutically acceptable carrier is compatible with the other ingredients of the composition, with the mode of administration, and not injurious to the patient. A pharmaceutically acceptable carrier may be either aqueous or non-aqueous. Pharmaceutically acceptable carriers include gums, starches, sugars, cellulosic materials, and mixtures thereof. Some examples of materials which can serve as pharmaceutically-acceptable carriers include, but are not limited to: (a) sugars, such as lactose, glucose and sucrose; (b) starches, such as corn starch and potato starch; (c) cellulose, and its derivatives, such as sodium carboxymethyl cellulose, ethyl cellulose and cellulose acetate; (d) powdered tragacanth; (e) malt; (f) gelatin; (g) talc; (h) excipients, such as cocoa butter and suppository waxes; (i) oils, such as peanut oil, cottonseed oil, safflower oil, sesame oil, olive oil, corn oil and soybean oil; (j) glycols, such as propylene glycol; (k) polyols, such as glycerin, sorbitol, mannitol and polyethylene glycol; (l) esters, such as ethyl oleate and ethyl laurate; (m) agar; (n) buffering agents, such as magnesium hydroxide, aluminum hydroxide, boric acid and sodium borate, and phosphate buffers; (o) alginic acid; (p) pyrogen-free water; (q) isotonic saline; (r) Ringer's solution; (s) ethyl alcohol; (t) phosphate buffer solutions; and (u) other non-toxic compatible substances suitable for use in pharmaceutical compositions.

The compositions of the invention may be administered using any means known in the art, including but not limited to oral, nasal, parenteral, topical, transdermal, or rectal routes of administration. Preferably, the compositions are adapted for oral or topical administration. For example, the active ingredient of the composition can be formulated with suitable excipients for the preparation of tablets, capsules, pellets, troches, lozenges, solutions, powders or granules, suspensions, hard or soft capsules, patches and any other suitable forms. The methods for preparing the pharmaceutical compositions and the selection of suitable excipients are known by a skilled person in the art.

The following Examples demonstrate some aspects of the invention. The Examples are not meant to limit the invention in any way.

EXAMPLE 1

A Randomized, Double-Blind, Placebo-Controlled Study for Diacerein Treatment on Albuminuria in Patients with Type 2 Diabetes Mellitus (DIA-DM01 Trial)

Objectives: To evaluate the efficacy and safety of diacerein for the treatment of albuminuria in patients with type 2 diabetes mellitus.

Primary Endpoints: To compare the change from baseline in the urinary albumin to creatinine ratio (UACR) after 24 weeks of diacerein or placebo administrated.

Subjects: Male or female type 2 diabetes patients (BMI≤35 kg/m$^2$) with micro-albuminuria.

Procedure: This was a Phase II, prospective, randomized, double-blind, and parallel comparison study comparing diacerein 50 mg bid (twice a day) versus placebo to albuminuria in patients with type 2 diabetes mellitus.

At the screening visit, patients who fulfilled the enrollment criteria and gave written informed consent entered a three to ten days screening period. During the screening period, the baseline UACR was evaluated. If the baseline UACR was greater than 50 mg/g, the patients were randomized into the 48-week treatment period in the 1:1 ratio (diacerein versus placebo). All participants were required to be taking stable dose of angiotensin-converting-enzyme (ACE) inhibitors, angiotensin receptor blockers (ARBs), or both, for three months prior to the study. These agents were continued throughout the trial. The hypoglycemic medications were maintained during the study period. The class and/or dosage were changed if clinically indicated. An introduction of a new treatment or any regimen change to the pre-existing co-medication that had hypoglycemic or hyperglycemic potential was allowed during the study with the consent of the clinical investigator.

The hyperuricemia sub-group was assembled from among the subjects with baseline blood uric acid level higher than 7.0 mg/dL. The results of blood uric acid level in the two treatment groups were analyzed by paired t-test of within-group changes.

The results are shown in Tables 1 and 2 below.

TABLE 1

Hyperuricemia Sub-group Evaluations in the Diacerein Group
Diacerein Group
Laboratory parameter: Uric Acid (mg/dL)

| | Baseline | week 12 | week 24 |
|---|---|---|---|
| N | 9 | 9 | 7 |
| Mean | 8.0667 | 6.6667 | 6.5571 |
| Change from baseline | | −1.40 | −1.34 |
| p value (week 12 or 24 vs. baseline) | | 0.0037 | 0.0060 |

TABLE 2

Hyperuricemia Sub-group Evaluations in the Placebo Group
Placebo Group
Laboratory parameter: Uric Acid (mg/dL)

|  | Baseline | week 12 | week 24 |
|---|---|---|---|
| N | 12 | 11 | 11 |
| Mean | 8.38 | 7.81 | 7.70 |
| Change from baseline |  | −0.59 | −0.80 |
| p value (week 12 or 24 vs. baseline) |  | 0.3887 | 0.2567 |

Subjects (n=76) with diabetic microalbinuria were randomized in a 1:1 ratio to receive twice-daily diacerein 50 mg (n=38), or placebo (n=38) for 24 weeks. The baseline blood levels of uric acid in nine subjects of the diacerein group (2 females and 7 males) and twelve subjects of the placebo group (2 females and 10 males) in the hyperuricemia sub-group were above 7.0 mg/dL, and the mean levels were 8.06 mg/dL and 8.38 mg/dL respectively.

After 12 weeks and 24 weeks of treatment, diacerein can significantly decrease the blood uric acid levels (Table 1, p value=0.0037 and 0.0060 in 12 and 24 week, respectively) compared with the baseline. Further, diacerein can maintain blood uric acid levels below the upper end of the normal range (i.e., below 7.0 mg/dL) during the treatment period. In contrast with the diacerein-treated group, the blood uric acid level was not improved in the placebo-treated group (Table 2, p value=0.3887 and 0.2567 in 12 and 24 week).

Figure 2:
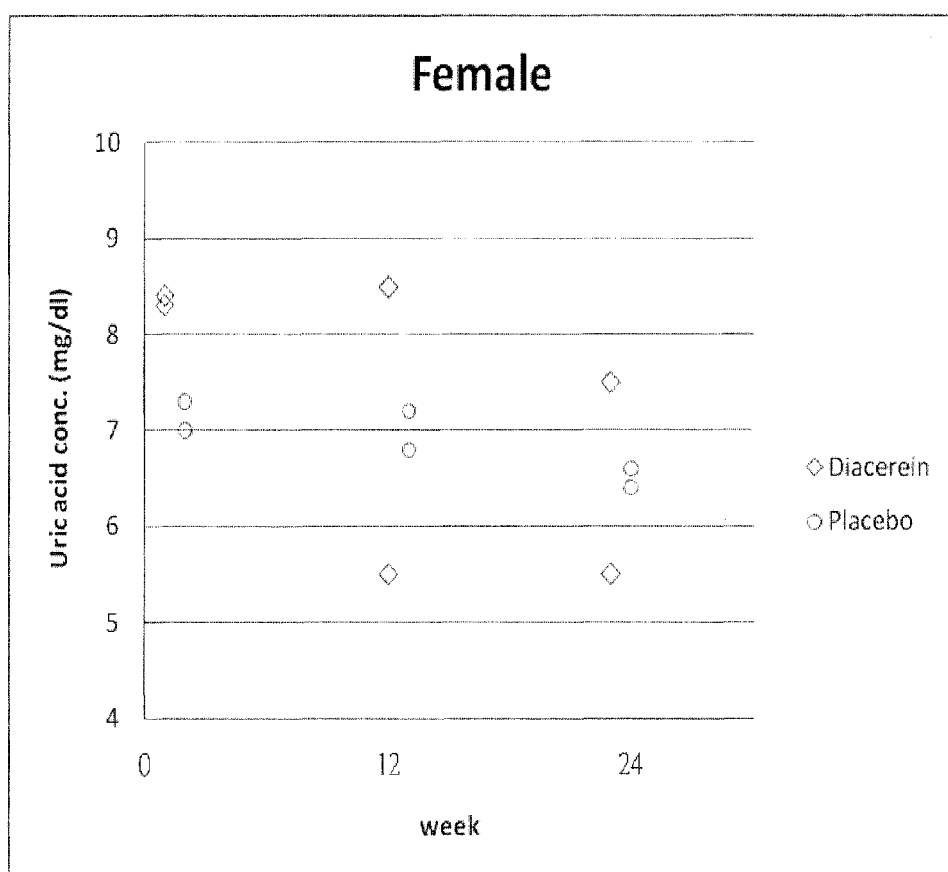
FIG. 2 is a graph demonstrating blood uric acid levels in female patients treated with either diacerein or placebo.

As Tables 1 and 2 demonstrate, in the beginning of the treatment, there were nine people in the diacerein group and twelve people in the placebo group. After 12 weeks of diacerein treatment, the blood uric acid levels in six of the nine patients achieved normal range (the level of uric acid in the blood in one female was below 6.0 mg/dL and the levels of uric acid in the blood in five males were below 7.0 mg/dL). In contrast, only one of the remaining eleven patients in the placebo group achieved the normal range (the level of uric acid in the blood in one male was below 7.0 mg/dL). The same trend was also observed in the 24-week treatment with diacerein and placebo. The levels of uric acid in the blood in four of the remaining seven patients of the diacerein group achieved the normal range (the level of uric acid in the blood in one female was below 6.0 mg/dL and the levels of uric acid in the blood in three males were below 7.0 mg/dL), while only three of the remaining eleven patients in the placebo group achieved the normal range (blood uric acid level in three males were below 7.0 mg/dL). FIGS. 1 and 2 further illustrate the results of the studies: FIG. 1 is a graph demonstrating blood uric acid levels in male patients treated with either diacerein or placebo; and FIG. 2 is a graph demonstrating blood uric acid levels in female patients treated with either diacerein or placebo.

These results strongly suggest that diacerein can significantly reduce the blood uric acid levels in patients with hyperuricemia and maintain the uric acid levels in the normal range over the course of the treatment period.

EXAMPLE 2

Case Study of Diacerein and Allopurinol Combination Therapy in Subjects with Chronic Gout and Hyperuricemia In DIA-DM01 trial described in Example 1, two subjects enrolled in the diacerein group had chronic gout history and were currently treating with allopurinol.

Case 1: A 70-year-old woman with history of chronic gout and hyperuricemia was treated with allopurinol since Jan. 2, 2009. Before she was enrolled in the diacerein trial, her medical treatment was unsatisfactory, and her blood level of uric acid was 8.3 mg/dL in visit 1 (Jul. 8, 2009).

After 24 weeks of the diacerein "add-on" treatment, the patient's blood uric acid level was lowered to 7.5 mg/dL. No acute flares were observed during the treatment period.

Case 2: A 66-year-old man with history of chronic gout and hyperuricemia was treated with allopurinol since Aug. 27, 2009. Before he was enrolled in the diacerein trial, his medical treatment was also unsatisfactory, and his blood level of uric acid was 9.5 mg/dL in visit 1 (Dec. 18, 2009).

After 12 weeks of the diacerein "add-on" treatment, the patient's blood uric acid level was reduced to 6.4 mg/dL and was maintained below the upper end of the normal range.

What is claimed is:

1. A method of treating hyperuricemia or a metabolic disorder associated with hyperuricemia, wherein said metabolic disorder associated with hyperuricemia is selected from the group consisting of acute gout, chronic gout, gout flares, uric acid nephrolithiasis and gouty nephropathy, consisting of: a) a step of administering to a patient in need thereof a therapeutically effective amount of a compound selected from the group consisting of: 1) diacerein, 2) rhein, 3) monoacetylrhein, and 4) a pharmaceutically acceptable salt or a prodrug thereof; and, optionally, b) a step of administering to said patient a urate-lowering therapeutic agent, wherein said method lowers blood levels of uric acid in said patient.

2. The method of claim 1, wherein said therapeutically effective amount of said compound is equivalent to 10 to 200 mg of diacerein base per day.

3. The method of claim 1, wherein said method decreases inflammatory effects of gout arthritis and gout flares induced by hyperuricemia; and/or dissolves kidney stones; and/or reduces the recurrence rate of acute inflammatory arthritis induced by hyperuricemia; and/or slows down the progression of urate nephropathy in said patient.

4. The method of claim 1, wherein said urate-lowering therapeutic agent is selected from the group consisting of xanthine oxidase inhibitors, uricosuric agents, urate oxidases, urinary alkalinizers and fenofibrate.

5. A method of improving blood uric acid level control in a patient with gout or hyperuricemia, consisting of: a) a step of administering to said patient a therapeutically effective amount of a compound selected from the group consisting of: 1) diacerein, 2) rhein, 3) monoacetylrhein, and 4) a pharmaceutically acceptable salt or a prodrug thereof; and, optionally, b) a step of administering to said patient a urate-lowering therapeutic agent, wherein said method lowers blood levels of uric acid in said patient.

6. The method of claim 2, wherein said therapeutically effective amount of said compound is equivalent to 10 to 200 mg of diacerein base per day.

7. A method of treating hyperuricemia or a metabolic disorder associated with hyperuricemia, wherein said metabolic disorder associated with hyperuricemia is selected from the group consisting of acute gout, chronic gout, gout flares, uric acid nephrolithiasis and gouty nephropathy, in a patient receiving a urate-lowering agent, consisting of: a) a step of administering to said patient a therapeutically effective amount of a compound selected from the group consisting of: 1) diacerein, 2) rhein, 3) monoacetylrhein, and 413) a pharmaceutically acceptable salt or, an analog, a prodrug thereof, and wherein said method lowers blood levels of uric acid in said patient.

8. The method of claim 7, wherein said therapeutically effective amount of said compound is equivalent to 10 to 200 mg of diacerein base per day.

9. The method of claim 7, wherein said urate-lowering agent is selected from the group consisting of the group consisting of xanthine oxidase inhibitors, uricosuric agents, urate oxidases, urinary alkalinizers and fenofibrate.

10. The method of claim 7, wherein said method decreases inflammatory effects of gout arthritis and gout flares induced by hyperuricemia; and/or dissolves kidney stones; and/or reduces the recurrence rate of acute inflammatory arthritis induced by hyperuricemia; and/or slows down the progression of urate nephropathy in said patient.

11. A method of treatment for hyperuricemia or a metabolic disorder associated with hyperuricemia, wherein said metabolic disorder associated with hyperuricemia is selected from the group consisting of acute gout, chronic gout, gout flares, uric acid nephrolithiasis and gouty nephropathy, in a patient with poor tolerance to therapeutic agents selected from the group consisting of anti-inflammatory agents and urate-lowering agents, consisting of: a) a step of administering to said patient a therapeutically effective amount of a compound selected from the group consisting of: 1) diacerein, 2) rhein, 3) monoacetylrhein, and 4) a pharmaceutically acceptable salt or a prodrug thereof; and, optionally, b) a step of administering to said patient a urate-lowering therapeutic agent, wherein said method lowers blood levels of uric acid in said patient.

12. The method of treatment of claim 11, wherein said method decreases inflammatory effects of gout arthritis and gout flares induced by hyperuricemia; and/or dissolves kidney stones; and/or reduces the recurrence rate of acute inflammatory arthritis induced by hyperuricemia; and/or slows down the progression of urate nephropathy in said patient.

13. The method of treatment of claim 11, wherein said therapeutically effective amount of said compound is equivalent to 10 to 200 mg of diacerein base per day.

* * * * *